United States Patent [19]

Nichols

[11] Patent Number: 4,728,504
[45] Date of Patent: Mar. 1, 1988

[54] STACKABLE MEDICAL INSTRUMENT STERILIZER CONTAINER

[76] Inventor: Robert L. Nichols, 808 Fort Worth, Jacksonville, Tex. 75766

[21] Appl. No.: 718,293

[22] Filed: Apr. 1, 1985

Related U.S. Application Data

[63] Continuation-in-part of Ser. No. 668,090, Nov. 5, 1984, Pat. No. 4,617,178.

[51] Int. Cl.⁴ .............................................. B65D 51/16
[52] U.S. Cl. ..................................... 422/297; 206/366; 206/439; 206/504; 220/371; 422/300; 422/310
[58] Field of Search ...................... 422/26, 27, 28, 297, 422/300, 310; 206/363, 364, 365, 366, 439, 504, 508, 509, 511; 220/371

[56] References Cited

U.S. PATENT DOCUMENTS

| | | | |
|---|---|---|---|
| 3,437,423 | 4/1969 | Mondiadis | 206/511 |
| 3,890,096 | 6/1975 | Nichol et al. | 206/511 X |
| 4,042,111 | 8/1977 | Smith | 206/511 X |
| 4,124,141 | 11/1978 | Armentrout et al. | 220/371 X |
| 4,271,973 | 6/1981 | Quagliaro et al. | 220/371 X |
| 4,372,921 | 2/1983 | Sanderson et al. | 422/300 |
| 4,396,583 | 8/1983 | Leboeuf | 220/371 X |
| 4,416,417 | 11/1983 | Sanderson et al. | 236/92 R |
| 4,458,815 | 7/1984 | Mollman et al. | 206/511 |
| 4,485,924 | 12/1984 | Ripoll et al. | 206/511 |
| 4,512,498 | 4/1985 | Leibinger | 222/366 |
| 4,551,311 | 11/1985 | Lorenz | 422/310 X |

Primary Examiner—Barry S. Richman
Assistant Examiner—William R. Johnson
Attorney, Agent, or Firm—Jerry W. Mills; Jefferson Perkins; Alan W. Lintel

[57] ABSTRACT

A medical instruments sterilization container (10) includes a housing (12) and a removable dome-shaped lid (14) having a filtered inlet port (18) disposed therethrough for permitting the passage of gas or steam into housing (12). A removable tray (16) is adapted to be disposed within housing (12) to hold various instruments to be sterilized and includes apertures (24) formed on the bottom of the tray for permitting condensate to drain therefrom. The bottom surface of housing (12) is sloped to two locations centered on opposite sides thereof and includes filtered outlet ports (40, 42) positioned at the two locations to permit discharged air and condensate to exit housing (12). Pedestals (30) are secured on the bottom surface of housing (12) to facilitate stacking of a plurality of sterilization containers.

9 Claims, 3 Drawing Figures

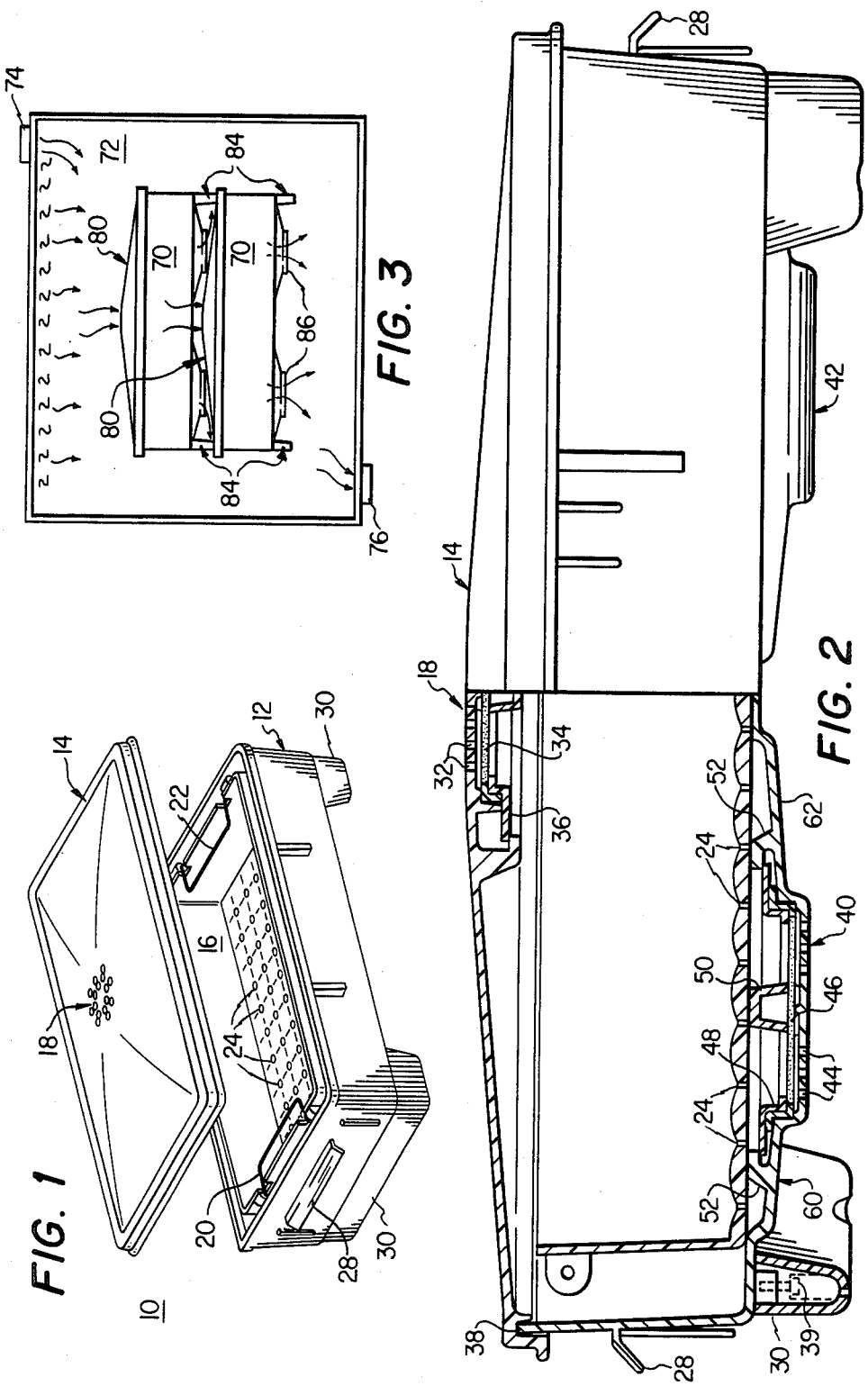

STACKABLE MEDICAL INSTRUMENT STERILIZER CONTAINER

CROSS REFERENCE TO RELATED APPLICATIONS

This application is a continuation-in-part of Ser. No. 668,090, filed Nov. 5, 1984, now U.S. Pat. No. 4,617,178, issued Oct. 14, 1986.

TECHNICAL FIELD

This invention relates to sterile containers generally and more particularly to a medical instrument sterilization container.

BACKGROUND OF THE INVENTION

It is necessary in hospital and other medical environments to sterilize medical instruments with steam or ethylene oxide. Various types of sterilization containers for medical instruments have therefore been developed. One such container comprises a plastic hermetically sealed housing having a tray disposed therein for receiving and organizing medical instruments. Filtered inlet and outlet ports are located on the top and bottom surfaces of the housing to permit the flow of steam through the container. The container is stackable and, thus in use, a plurality of such containers may be disposed within a steam sterilizer and arranged therein in a stack. That arrangement permits more instruments to be sterilized per sterilization cycle, thus lowering the sterilization cost per instrument. This process has, however, suffered from various disadvantages.

By way of explanation, steam sterilizers are normally designed so that steam enters the chamber of the sterilizer through an inlet port located at the top of the unit. As steam enters, colder air in the sterilizer is pressed toward the bottom of the sterilizer chamber and eventually exits the sterilizer through an outlet port located on the bottom surface of the sterilizer. When a plurality of sterilization containers are stacked within the sterilizer, steam entering the sterilizer chamber will enter the inlet port of the topmost sterilization container in the stack and be discharged through the outlet port of that container. The discharged steam will then enter the inlet port of the container located immediately therebeneath and will in turn enter and be discharged from each of the containers in the stack.

As steam successively enters each of the containers, it comes into contact with the medical instruments located in the container and gradually cools off. Thus, the discharged air and condensate will be colder than the original fresh steam and accordingly less effective in the sterilization process. Further, the steam becomes less sterile as it passes through succeeding containers. As the number of stacked containers increases, the problem of ineffective sterilization necessarily also increases. Prior containers have also often been designed so that condensate tends to collect within the containers instead of draining therefrom. The need has thus arisen for a plastic sterilization container which is stackable and which also enables the effective and economical sterilization of medical instruments.

BRIEF DESCRIPTION OF THE DRAWINGS

For a more complete understanding of the present invention and the objects and advantages thereof, reference is now made to the following description taken in conjunction with the accompanying Drawings in which:

FIG. 1 is a perspective view of the present sterilization container showing the lid in an exploded position;

FIG. 2 is a partially sectioned view of one-half of the length of the present sterilizer container; and, FIG. 3 is a schematical representation of a steam sterilizer with a pair of sterilization containers stacked therein.

SUMMARY OF THE INVENTION

In accordance with the present invention, a medical instrument sterilization container comprises a housing dimensioned to receive medical instruments for sterilization by gas or steam. A removable dome-shaped lid is provided which enables access to the housing and seals with the housing to maintain the sterility of the housing interior. The lid includes a filtered inlet port for permitting gas or steam to pass therethrough into the housing but preventing the passage of contaminates into the interior of the housing. The housing bottom is sloped to at least one location to drain condensate generated during the sterilization process to that location. A filtered outlet port is disposed in the housing bottom at each of the sloped locations for permitting condensate and air to exit the housing. Pedestals are also provided on the bottom surface of the housing to facilitate stacking of a plurality of sterilization containers.

It is an important aspect of the present invention that the lid is dome-shaped to a high point for the entrance of steam and is configured so that when a plurality of containers are stacked one upon the other, the inlet port of each container in the stack will project above the outlet port of the preceding container in the stack. Thus, fresh, i.e., non-discharged steam will enter the container located at each level, thereby eliminating the problems of conventional containers while allowing stacking inside a steam sterilizer in multiple levels.

DETAILED DESCRIPTION OF THE INVENTION

Referring now to the Drawings, wherein like reference numerals designate like or corresponding parts throughout the views, FIG. 1 is a perspective view of the sterilization container of the present invention. As shown in FIG. 1, sterilization container 10 comprises a housing 12 having a removable lid 14. A removable tray 16 is disposed within the housing 12 and is adapted to receive various medical instruments, such as knives, scissors and the like.

Lid 14 is substantially dome-shaped and includes an inlet port positioned at the highest point of the dome for permitting gas or steam to enter the housing. A filtered inlet port 18 is disposed through lid 14 at the location of the inlet port. Filtered inlet port 18 allows the passage of heated sterile air or steam therethrough but prevents the passage of bacteria or other contaminates into the interior of the container. Two additional filters, described hereinafter in greater detail, are disposed in the bottom of housing 12. Tray 16 includes removable metal handles 20 and 22 to enable easy withdrawal of the tray from the housing 12. Apertures 24 are disposed through tray 16 to allow the passage of steam and condensate therethrough. Metal clamps (not shown) are attached on both sides of housing 12 and are manually movable to clamp against the sides of lid 14 to thus lock the lid in place on the housing. Suitable sealing surfaces are also provided between housing 12 and lid 14 to provide an essentially airtight container when the lid is clamped to the housing. Handles 28 are provided on the opposite ends of container 12 to facilitate handling of the container. Pedestals 30 are also provided on opposite ends of container 12 so that the container is self-supporting. Additionally, the pedestals facilitate the stacking of a plurality of sterilization containers one upon the other.

FIG. 2 illustrates a partially sectioned view of the sterilization container of the present invention. As shown in FIG. 2, filter 18 is disposed through lid 14 at the inlet port and includes apertures 32 which communicate with the atmosphere. A removable filter 34 is located below filter 18 and is clamped in place by a twistable cap 36. A sealing portion 38 is provided between housing 12 and lid 14 and is operative, as described above, to provide an airtight container.

With further reference to FIG. 2, pedestals 30 are shown. Pedestals 30 are removably secured to the housing bottom using screw members 39 disposed through a support member (not shown) located on each of the lateral side surfaces of the interior of the housing bottom. Pedestals 30 elevate the bottom of housing 12 and facilitate the stacking of a plurality of sterilization containers. Also disposed on the bottom of housing 12 are a pair of identical filters 40 and 42 which are also substantially identical to filter 18. Apertures 44 are disposed through the bottom of housing 12 in the area of filter 40. A removable filter 46 is positioned immediately beneath filter 40 and is held tightly in place by a twistable cap 48. A handle 50 is provided on the cap 48 to enable twisting into place. Catch members 52 inwardly extend from the bottom of housing 12 for abutting cap 48 to maintain filter 46 securely in place.

It is an important aspect of the present invention that the bottom of housing 12 slopes downwardly toward filters 40 and 42. Specifically, the bottom walls 60 and 62 each slope toward the location of filter 40 in different directions. Thus, condensate or moisture in the left-hand side of the tray of housing 12 will move by gravity to filter 40. Moisture and condensate on the right-hand side of the housing 12 will likewise move by gravity along similarly sloping housing bottom walls to filter 42. This domed configuration, in conjunction with apertures 24 in tray 16, causes condensate and discharged air to flow through the apertures 24 toward filters 40 and 42 and thus prevents the accumulation of condensate on the bottom of the container.

FIG. 3 illustrates the sterilization container in use. As shown in FIG. 3, a pair of sterilization containers 70 are disposed within a steam sterilizer 72. It will of course be understood that more than two stacked containers will often be used. Sterilizer 72 is a conventional sterilizer unit of the type commercially available and includes an inlet port 74 located on the top surface thereof for permitting the entry of steam or gas into the sterilizer unit. An outlet port 76 is provided on the bottom surface of sterilizer 72 for allowing air and condensate to exit the sterilizer. Sterilization containers 70 are substantially identical to container 10 described above with respect to FIGS. 1 and 2. Thus, each of containers 70 includes a removable lid 80 having a filtered inlet port disposed therethrough for permitting the passage of the air into the container, a pair of pedestals 84, and a pair of filtered outlet ports 86. As described hereinabove with respect to FIG. 1, the bottom surface of the container is sloped on either side thereof in different directions toward the filtered outlet ports. Moisture and condensate are thus moved toward the outlet ports and are discharged therethrough.

As best seen in FIG. 3, the containers are specially designed with the lid being dome-shaped to a high point for the entry of steam and are configured so that when a plurality of containers are stacked one upon the other, the inlet port of each of the containers in the stack will project above the outlet port of the container located immediately above it. Thus the discharged air and condensate of the upper container will not be permitted to enter the inlet port of a lower container. Fresh steam will thus enter the inlet ports of the sterilization containers at each level, thereby eliminating the problems of conventional containers and allowing stacking of sterilization containers in multiple levels inside the steam sterilizer. As shown in FIG. 3, the bottom outlet ports 86 are spaced laterally from the filtered inlet port 18 of the lower container, thus insuring that the discharged air does not contaminate the fresh steam entering each container.

Whereas the present embodiment has been described in detail, it should be understood that various changes, alterations and substitutions can be made therein without departing from the spirit and scope of the invention as defined in the appended claims.

What is claimed is:

1. A medical instrument sterilization container comprising:
   a housing having a bottom and sidewalls and dimensioned for receiving medical instruments for sterilization by gas or steam, said housing bottom sloping to at least one location to drain condensate generated during the sterilization process to said at least one location;
   at least one pedestal member coupled to said housing bottom for supporting the container and for interacting with a portion of another similarly constructed container to permit stacking of a plurality of containers;
   a removable dome-shaped lid for said housing for enabling access to said housing and for creating a sealed volume therein to thus maintain the sterility of the interior of said housing;
   one filtered outlet port disposed in said housing bottom at each of said at least one location for allowing the passage of condensate therethrough and for also allowing air compressed toward the housing bottom by the passage of steam through said lid to exit said housing; and
   a filtered inlet port disposed at the highest point of said lid for allowing the passage of the sterilizing gas or steam therethrough, said inlet port disposed at a height such that it is vertically above and laterally offset from each of said at least one outlet port of an upper container when a plurality of containers are arranged in a stacked configuration.

2. The sterilization container of claim 1 wherein said filtered inlet port comprises a disposable filter element removably sealed in said lid.

3. The sterilization container of claim 1 wherein said filtered outlet port comprises a disposable filter element removably sealed in said housing bottom.

4. The sterilization container of claim 1 further comprising a removable tray for receiving medical instruments, the bottom of said tray including apertures therethrough.

5. The sterilization container of claim 1 wherein said housing bottom slopes to two locations centered on opposite sides of the center thereof.

6. The sterilization container of claim 5 further comprising outlet ports at said two locations, having a filter disposed in said housing bottom in each of said outlet ports at said two locations.

7. A sterilization system for sterilizing medical instruments by gas or steam in a sterilizing chamber comprising:
   upper and lower containers configured to be stacked one upon another in a sterilizing chamber;
   each of said containers having a domed lid with a filtered inlet centered in the top thereof for receiving gas or steam and further having filtered outlets on the bottom thereof, said outlets being vertically and laterally spaced from said inlet such that steam or gas exhausting from said upper container exits said upper container at a point vertically below and laterally offset from the inlet of said lower container and thus does not enter the inlet of said lower container.

8. The sterilization system of claim 7 and further comprising pedestals on the bottom of each container for spacing the bottom of each container above said inlet of a lower stacked container.

9. A sterilization system for sterilizing medical instruments by gas or steam comprising:
   a gravity steam sterilizer having a chamber, said chamber including an inlet port disposed proximate the top of said chamber for permitting the passage of condensate and air generated during the sterilization process to exit said sterilizer;
   a plurality of sterilization containers for being disposed in said chamber and arranged therein in a stack, each of said sterilization containers comprising:
     a housing having a bottom and side walls and dimesioned for receiving medical instruments therein;
     a removable dome-shaped lid for enabling access to said housing and for creating a sealed volume therein to thus maintain the sterility of the interior of said housing;
     a filtered inlet port disposed on top of said lid for allowing the passage of gas therethrough;
     said housing bottom sloping to at least one location to drain condensate to said at least one location;
     a filtered outlet port disposed in said housing bottom at each of said at least one location to allow the passage of condensate therethrough and for also allowing air compressed toward the housing bottom by the passage of steam through the lid to exit said housing;
     a pair of pedestal members for being coupled to the housing bottom on either side thereof for supporting the container and enabling stacking of a plurality of containers by cooperating with a lid of another container; and
     said domed lid and said sloping bottom dimensioned so that the inlet port of a lower container on said stack is positioned at a higher elevation than, and laterally offset from, the outlet port of the container immediately above said lower container throughout the sterilization process.

* * * * *